(12) United States Patent
Foster et al.

(10) Patent No.: US 9,555,185 B2
(45) Date of Patent: Jan. 31, 2017

(54) BIOMEDICAL HAEMOSTATIC POWDER DISPENSER

(75) Inventors: Clark Foster, Mission Viejo, CA (US); David Mishelevich, Playa Del Rey, CA (US); Eric Warner, Oceanside, CA (US); Aaron Gifford, Lake Elsinore, CA (US)

(73) Assignee: BIOM'UP, Saint-Priest (FR)

( * ) Notice: Subject to any disclaimer, the term of this patent is extended or adjusted under 35 U.S.C. 154(b) by 546 days.

(21) Appl. No.: 14/007,794

(22) PCT Filed: Apr. 26, 2012

(86) PCT No.: PCT/EP2012/057641
§ 371 (c)(1),
(2), (4) Date: Sep. 26, 2013

(87) PCT Pub. No.: WO2012/146652
PCT Pub. Date: Nov. 1, 2012

(65) Prior Publication Data
US 2014/0018729 A1   Jan. 16, 2014

Related U.S. Application Data

(60) Provisional application No. 61/479,805, filed on Apr. 27, 2011.

(30) Foreign Application Priority Data

Apr. 27, 2011  (EP) .................................... 11163820

(51) Int. Cl.
*A61M 13/00*   (2006.01)
*A61M 5/00*    (2006.01)
(Continued)

(52) U.S. Cl.
CPC ............. *A61M 5/00* (2013.01); *A61M 5/3015* (2013.01); *A61B 2017/00522* (2013.01);
(Continued)

(58) Field of Classification Search
CPC ............. A61M 2205/8225; A61M 2205/8218; A61M 5/2046; A61M 2005/006; A61M 5/3015; A61M 5/2053; A61M 2005/005; A61M 5/30; A61M 2202/064; A61M 11/06
See application file for complete search history.

(56) References Cited

U.S. PATENT DOCUMENTS 2,017,276 A * 10/1935 Ericson .................. A61M 5/24
604/143
5,584,807 A * 12/1996 McCabe ................ C12M 35/00
604/24
(Continued)

FOREIGN PATENT DOCUMENTS

CN   1649813 A   8/2005
EP   1 550 713 A2   7/2005
(Continued)

OTHER PUBLICATIONS

Extended European Search Report, dated Oct. 14, 2011, for Patent Application No. 11163820.1.
(Continued)

*Primary Examiner* — Emily Schmidt
(74) *Attorney, Agent, or Firm* — Birch, Stewart, Kolasch & Birch, LLP

(57) ABSTRACT

A biomedical haemostatic powder dispenser (1) by which individual doses of powdered medication that are stored in respective chambers of a rotatable carousel (22) are fluidized for delivery to a targeted treatment site (e.g., a wound in order to stop bleeding). In particular, a squeeze handle (7) is
(Continued)

activated (i.e., depressed) so as to cause a blast of gas under pressure to be applied from a gas reservoir (30) to a particular one of the powder-filled chambers of the medication carousel so that a single measured dose of medication is entrained and delivered to the patient. At the same time that the squeeze handle is activated, the medication carousel is rotated so that a different powder-filled chamber is moved within a fluid path between the gas reservoir and an outlet nozzle tube (10) of the dispenser and a kit for dispensing a powder.

20 Claims, 10 Drawing Sheets

(51) Int. Cl.
*A61M 5/30* (2006.01)
*A61M 5/20* (2006.01)
*A61B 17/00* (2006.01)

(52) U.S. Cl.
CPC .. *A61B 2017/00544* (2013.01); *A61M 5/2053* (2013.01); *A61M 2005/005* (2013.01); *A61M 2202/064* (2013.01)

(56) References Cited

U.S. PATENT DOCUMENTS

| | | |
|---|---|---|
| 5,656,035 A | 8/1997 | Avoy |
| 6,273,861 B1 | 8/2001 | Bates et al. |
| 2005/0215452 A1 | 9/2005 | Ruland et al. |
| 2008/0021374 A1* | 1/2008 | Kawata ............ A61B 17/00491 604/23 |

FOREIGN PATENT DOCUMENTS

| | | |
|---|---|---|
| EP | 1 745 747 A1 | 1/2007 |
| FR | 2 863 503 A1 | 6/2005 |
| KR | 10-2004-0052811 A | 6/2004 |
| WO | WO 2005/072700 A2 | 8/2005 |
| WO | WO 2007/030776 A2 | 3/2007 |

OTHER PUBLICATIONS

International Search Report and Written Opinion of the International Searching Authority (PCT/ISA/210 and PCT/ISA/237), dated Jul. 30, 2012, for International Application No. PCT/EP2012/057641.

\* cited by examiner

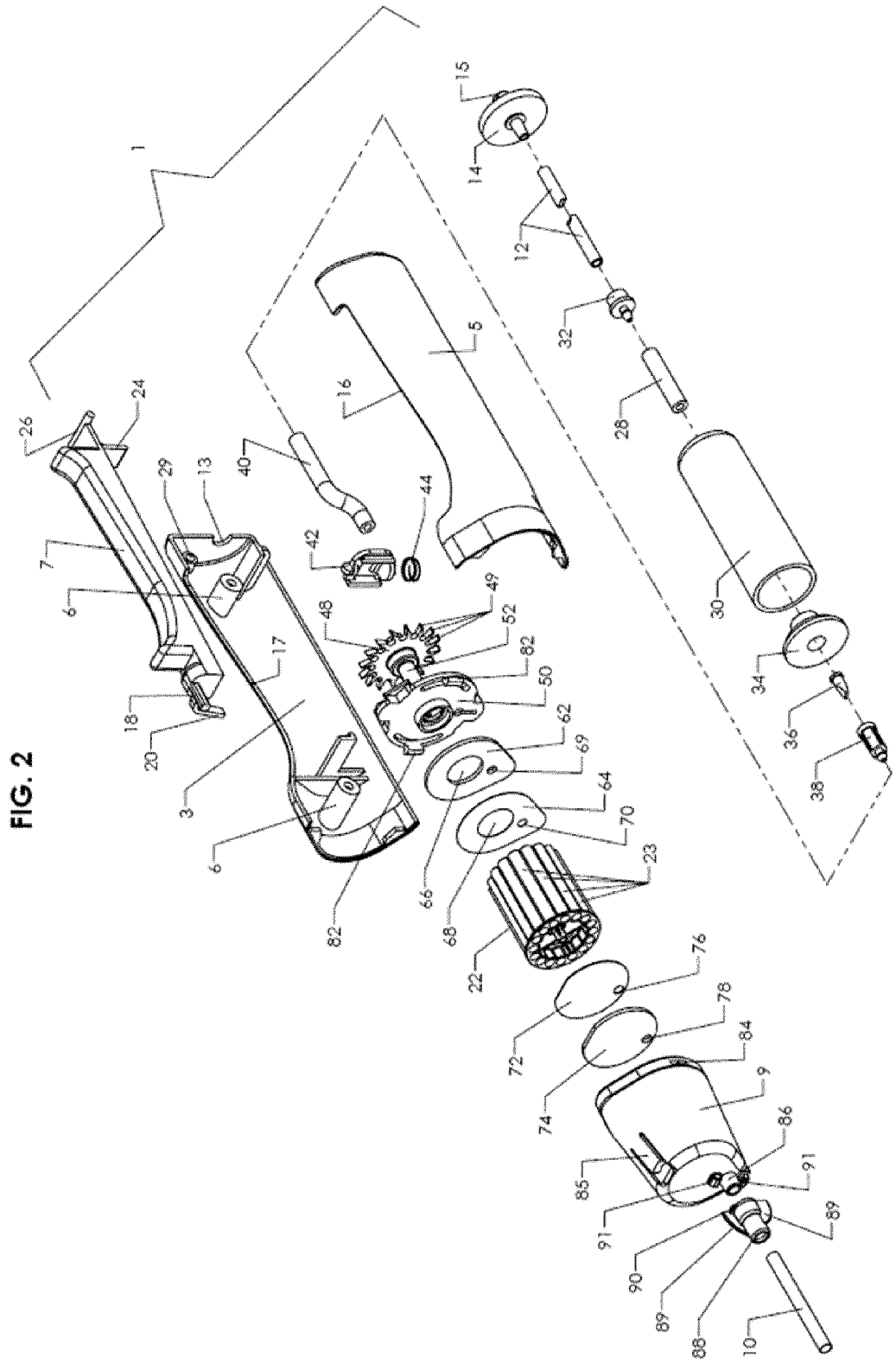

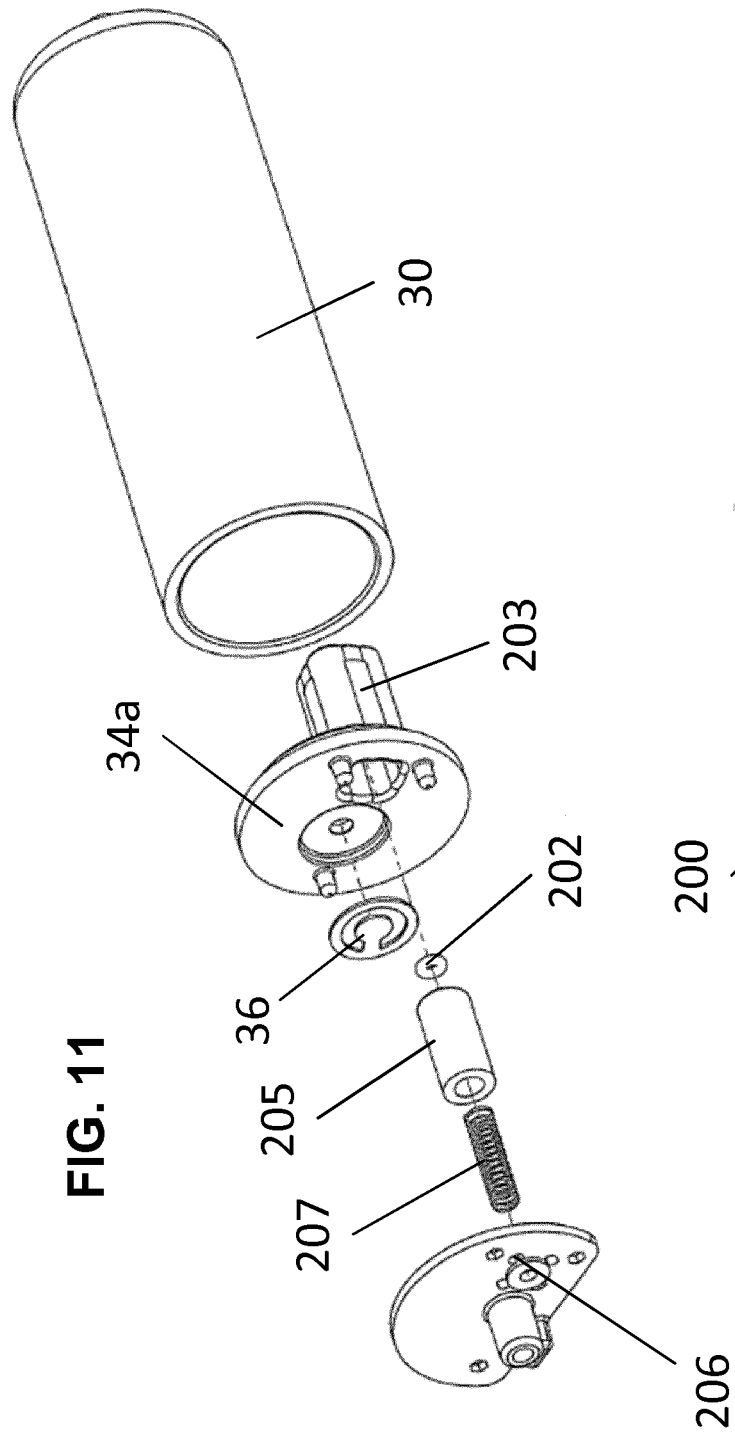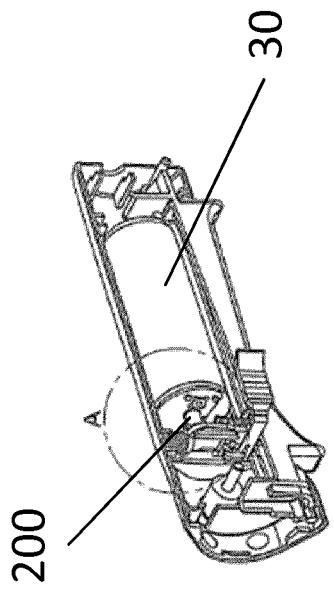
FIG. 11
FIG. 10

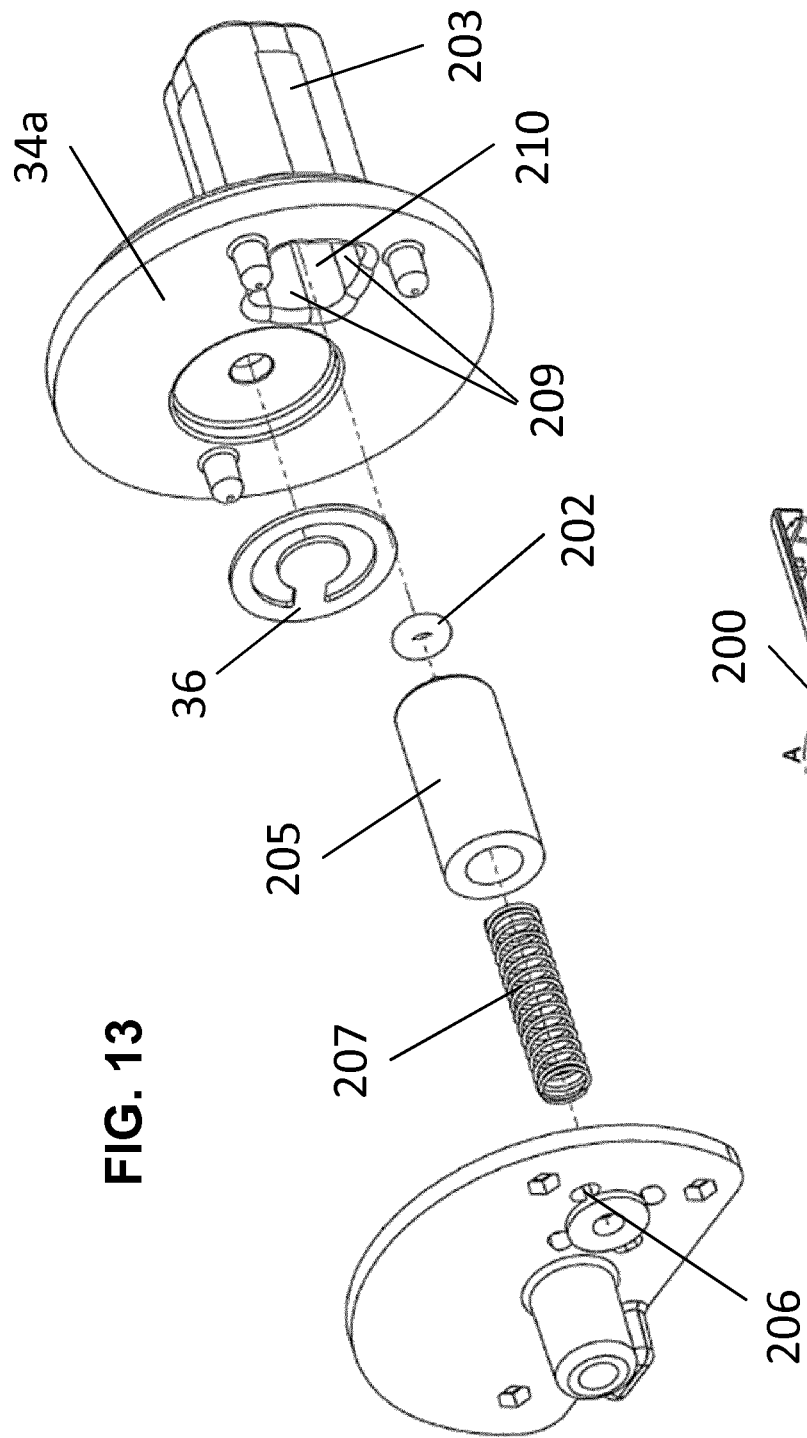
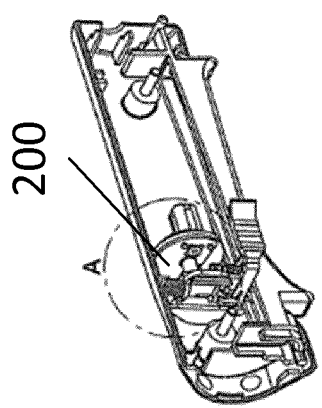
FIG. 13
FIG. 12

BIOMEDICAL HAEMOSTATIC POWDER DISPENSER

CROSS REFERENCE TO RELATED APPLICATIONS

This application is the National Phase of PCT/EP2012/057641 filed on Apr. 26, 2012, which claims priority under 35 U.S.C. 119(e) to U.S. Provisional Application No. 61/479,805 filed on Apr. 27, 2011 and under 35 U.S.C. 119(a) to Patent Application No. 11163820.1 filed in Europe on Apr. 27, 2011, all of which are hereby expressly incorporated by reference into the present application.

FIELD OF THE INVENTION

The invention relates to the field of delivery systems adapted for spraying powdered medication, in particular dispenser for delivering biomedical hemostatic powder.

TECHNICAL BACKGROUND

At times, it becomes necessary to deliver a powdered medication to a patient undergoing treatment. By way of example, such a powdered medication may be especially useful to create a cushion patch and/or to suppress bleeding at a tissue wound site.

When the powdered medication is stored in a single container, it is often difficult for a healthcare worker to accurately measure the precise dosage to be administered. Consequently, the patient may receive an excess or too little of the medication. Thus, the delivery process may be inconsistent and not easily repeatable. Moreover, a large supply of powdered medication stored in a single container over a long period of time may result in settling and stratification of the powder.

Some devices have been disclosed that are adapted for delivery of material stored in individual cartridges, each cartridge having a single dose of the material to be delivered. The device disclosed in European patent application EP 1 550 713 comprises a multi-cartridge holder arranged cylindrically in the device. However, such device is adapted for delivering genetic material of a very small size into living tissue. Indeed, the powdered material that is to be delivered with such a device is of a size ranging from 0.2 μm to 3 μm, which is thus far away from the specifications of powdered medication, wherein the powder is generally of a size of dozens or hundreds of micrometers. The structure and operation of such device is thus not adapted for delivering powdered medication.

Difficulty may also arise when attempting to accurately deliver a precise dose of powdered medication where the tissue site is not easily accessible, such as in the case when a laparoscopic delivery technique will be employed. Accordingly, it would be desirable to have access to a dispenser by which a precise dose of powdered medication can be accurately and repeatedly delivered to a tissue site requiring treatment.

SUMMARY OF THE INVENTION

This invention relates to a biomedical haemostatic powder dispenser by which multiple precise doses of powdered medication are stored in individual chambers of a rotatable medication carousel to be accessed and delivered to a patient. When the powder dispenser is activated, a blast of gas under pressure is supplied to a particular one of the powder-filled chambers of the medication carousel so that a single measured dose is entrained and delivered to the patient under the control of a squeeze handle.

More precisely, it is proposed a device for delivering a powder as described in the appended claims.

Following a first aspect, the invention has for subject matter a device for delivering a powder to a target site, said device comprising:
- a body, which may comprise two shells;
- a powder storage, in particular a medication carrousel, filled with the powder to be delivered to the target site;
- a gas reservoir located within said body, in particular intended to be filled with a gas under pressure;
- an outlet nozzle communicating with said powder storage;
- a normally closed gas outlet valve, in particular a normally closed gas outlet pinch valve, located within said body between said gas reservoir and said powder storage and being closed to block the flow of gas under pressure from said gas reservoir to said powder storage; and
- an activation handle, in particular a squeeze handle, coupled to said normally closed gas outlet valve, said activation handle moving in a first direction relative to said body in response to a force applied to said activation handle for causing said normally closed gas outlet valve to open and thereby enable a blast of gas under pressure to be applied from said gas reservoir to said powder storage, whereby at least some of the powder from said powder storage is entrained and delivered to the target site by way of said outlet nozzle.

The expression "normally closed gas valve", in the sense of the invention, means that the valve is closed when no force is applied to the device, and in particular to the activation handle.

The expression "normally open gas valve", in the sense of the invention, means that the valve is open when no force is applied to the device, and in particular to the activation handle. Following an embodiment the normally open gas valve is closed the device is not plugged to the gas source or when the device is actuated More particularly, the normally open valve may switch to closed and the normally closed valve may switch to open at the same moment and only in response to the movement of the activation handle.

The gas source may be a network of gas under pressure, e.g. those which are present in hospitals with plugs in the room, or can be a can of gas under pressure which may be movably incorporated in the device. In the last case, the device may be autonomous.

The device may be able to deliver several shots of powder, for example 2 to 20.

Preferable but not limited aspects of such powder dispenser, taken alone or in combination, are as follows.

The device may further comprise a gas outlet hose running between said gas reservoir and said powder storage, said normally closed gas outlet valve coupled to said gas outlet hose and being closed so as to shut said gas outlet hose and thereby block the flow of gas under pressure from said gas reservoir to said powder storage, and said normally closed outlet valve being opened in response to the movement of said activation handle in said first direction so that said gas outlet hose is correspondingly opened to allow said blast of gas under pressure to be applied from said gas reservoir to said powder storage via said gas outlet hose.

In particular, the normally closed gas outlet valve surrounds said gas outlet hose, said normally closed gas outlet valve having stationary, in particular an anvil, and movable, in particular a clamp, valve members between which said gas outlet hose is positioned, said stationary and movable valve members being positioned together when said normally closed gas outlet valve is closed in order to shut said gas outlet hose, and said stationary and movable valve members being positioned apart when said normally closed gas outlet valve is opened to correspondingly open said gas outlet hose.

The device may further comprise a spring located within said body and communicating with said normally closed gas outlet valve, said spring being compressed when said activation handle moves in said first direction relative to said body in response to the force applied to said handle for causing the stationary and movable valve members of said normally closed gas outlet valve to be positioned apart and said outlet valve to be opened, and said spring expanding when the force applied to said activation handle is terminated for causing said stationary and movable valve members to be positioned together and said outlet valve to be closed.

The device may comprise a spring surrounding the movable valve member of said normally closed gas outlet valve, said spring generating a pushing force against said movable valve member for urging said movable valve member to move relative to said stationary valve member and said activation handle to rotate in an opposite direction relative to said body when the force applied to said handle is terminated and said spring expands.

The activation handle may be depressed and rotated inwardly of said body when said handle moves in said first direction relative to said body in response to the force applied to said handle.

The device may comprise a pivot pin attached to said activation handle and a pivot post attached to said body within which said pivot post is pivotally received, said pivot pin rotating at said pivot post and said activation handle rotating inwardly of said body when said handle moves in said first direction in response to the force applied thereto.

The device may comprise a normally open gas inlet valve, in particular a pinch valve, more particularly comprising a movable part and a stationery part, located within said body between said gas reservoir and a source of gas under pressure, said normally open gas inlet valve being opened to permit said gas reservoir to be filled with the gas under pressure from the source thereof, said activation handle being coupled to said normally open gas inlet valve to cause said normally open gas inlet valve to close and thereby prevent said gas reservoir from being filled with the gas under pressure from said source when said activation handle moves in said first direction relative to said body in response to said force applied to said activation handle.

The device may comprise a gas inlet hose, in particular a gas inlet tube, attached at one end thereof to said gas reservoir and adapted to be connected at the opposite end to the source of gas under pressure, said normally open gas inlet valve being coupled to said gas inlet hose and being closed in response to the force applied to said activation handle and the movement of said activation handle in said first direction so as to shut said gas inlet hose and thereby block the flow of gas under pressure from said source thereof to said gas reservoir via said gas inlet hose, and said normally open gas inlet valve being opened when the force applied to said activation handle is terminated so that said gas inlet hose is correspondingly opened to allow said gas reservoir to be filled with the gas under pressure from said source via said gas inlet hose.

The device may comprise a normally open gas inlet valve including a hose pinching member attached to and movable with said activation handle, said hose pinching member moving towards and into contact with said gas inlet hose so that said gas inlet hose is shut and the flow of gas under pressure from said source thereof to said gas reservoir via said gas inlet hose is blocked when said activation handle moves in said first direction in response to the force applied thereto.

The device may comprise a powder storage including a plurality of powder-filled chambers, each chamber being filled with a supply of powder to be delivered to the target site, a particular one of said powder-filled chambers of said powder storage being located in a fluid path between said gas reservoir and said outlet nozzle so that the powder contents of said particular one chamber is entrained by said blast of gas when said activation handle is moved in said first direction in response to the force applied thereto.

The device may comprise a powder storage which is rotatable to be positioned so that only the particular one of said plurality of powder-filled chambers of said powder storage is located in said fluid path.

The device may comprise a ratchet wheel located within said body and coupled to said powder storage, said ratchet wheel being rotated in response to said activation handle moving in said first direction relative to said body in response to the force applied to said handle for imparting a corresponding rotation to said powder storage until the particular one of said plurality of powder-filled chamber is rotated into said fluid path.

The device may further comprise a ratchet actuator projecting from said activation handle and communicating with said ratchet wheel, such that a movement of said activation handle in said first direction causes a corresponding movement of said ratchet actuator and a rotation of each of said ratchet wheel and said powder storage to which said ratchet wheel is coupled, whereby the particular one of said plurality of powder-filled chambers of said powder storage is rotated into said fluid path.

The device may also further comprise a cover, in particular a carrousel cover, located between said body and said outlet nozzle and enclosing said powder storage, said cover having a back cap, in particular a carrousel back cap, extending thereacross and a hole formed through said back cap, said ratchet wheel coupled to said powder storage by way of a shaft extending through said hole and between said ratchet wheel and said powder storage, whereby a rotation of said ratchet wheel within said body is transferred to the powder storage enclosed by said cover by way of said shaft.

The device may comprise a back cap which is detachably connected to a cover by means of flexible snaps projecting from said back cap for the removable receipt by respective locking slots formed in said cover.

The device comprising a cover including a flexible index tab projecting therefrom and communicating with said powder storage enclosed by said cover, said index tab limiting the rotation of said powder storage so that successive ones of said plurality of powder filled chambers of said powder storage are moved one at a time into said fluid path between said gas reservoir and said outlet nozzle.

The device comprising a back cap of the cover having serially connected gas channels running horizontally and vertically therethrough, said gas channels lying in said fluid path between said gas reservoir and said outlet nozzle.

The device comprising a powder storage enclosed by a cover having at least one inlet seal extending across one end thereof to seal first ends of the plurality of powder-filled chambers of said powder storage and at least one outlet seal extending across the opposite end thereof to seal the opposite ends of said powder-filled chambers, each of said inlet and outlet seals having a hole formed therethrough and lying in said fluid path between said gas reservoir and said outlet nozzle.

The device for delivering a powder to a target site may comprise:

a normally open gas inlet valve located within said body between said gas reservoir and a source of gas under pressure and being opened to permit said gas reservoir to be filled with the gas under pressure from the source thereof; and an activation handle coupled to each of said normally closed gas outlet valve and said normally open gas inlet valve, said activation handle moving in a first direction relative to said body in response to a force applied to said activation handle for simultaneously causing said normally open gas inlet valve to close and thereby block said gas reservoir from being filled with the gas under pressure from said source and for causing said normally closed gas outlet valve to open and thereby enable a blast of gas under pressure to be applied from said gas reservoir to said powder storage, whereby at least some of the powder from said powder storage is entrained and delivered to the target site by way of said outlet nozzle.

In general terms, and according to a preferred embodiment, a biomedical haemostatis powder dispenser is disclosed which includes a rotatable medication carousel within which multiple precise doses of powdered medication are stored to be repeatedly dispensed one dose at a time to a patient. The carousel has a plurality of chambers, each of which containing a measured dose of powdered medication. The powder dispenser also includes a squeeze handle which initiates both a rotation of the medication carousel as well as a blast of gas under pressure for delivering one of the doses of powdered medication to the patient. The medication carousel is located and rotated within a carousel cover. An actuation finger carried by and movable with the squeeze handle is interfaced with the teeth of a ratchet wheel. The ratchet wheel is connected to the carousel by a shaft that runs through a center hole in a carousel back cap that is attached across the back of the carousel cover. Whenever the squeeze handle is depressed by the user to activate the powder dispenser, the actuation finger is moved by the handle towards and into contact with the teeth of the ratchet wheel to impart a rotation to the ratchet wheel. A rotation of the ratchet wheel causes a corresponding rotation of the medication carousel within the carousel cover in order to move successive ones of the medication-filled chambers of the carousel into a fluid path so that the contents of a particular chamber can be accessed and discharged from the powder dispenser by way of an outlet nozzle tube.

A gas reservoir is filled with a known volume of compressed gas from an external supply thereof by way of a reservoir inlet hose. A normally-open inlet pinch valve which is carried by and movable with the squeeze handle engages the reservoir inlet hose. A gas outlet hose extends from the gas reservoir to horizontal (i.e., inward) and vertical (i.e., upward) channels of the carousel back cap. A normally-closed, spring-biased gas outlet pinch valve surrounds and engages a gas outlet hose from the reservoir. The channels of the back cap communicate with one side of the particular chamber of the medication carousel from which powdered medication is to be dispensed via axially-aligned inlet holes formed through a pair of sliding inside gaskets which seal the rear of the carousel. The opposite side of the particular medication-filled chamber communicates with the outlet nozzle tube of the dispenser via axially-aligned outlet holes formed through a pair of sliding outside gaskets which seal the front of the medication carousel.

With the biomedical haemostatic powder dispenser in an at-rest condition, no squeezing force is applied by the user to the squeeze handle. In this case, the normally-open inlet pinch valve remains open so that the gas reservoir is filled with compressed gas through the reservoir inlet hose from the external gas supply. The normally closed gas outlet pinch valve remains closed so as to pinch shut the gas outlet hose and thereby prevents the flow of gas to flow from the gas reservoir to the medication carousel.

In order to deliver a dose of powdered medication from the medication carousel of the medication dispenser to the patient during an activated condition, a squeezing force is applied to the squeeze handle, whereby the handle is depressed and rotated at a pivot pin. A depression of the squeeze handle moves the inlet pinch valve carried by the handle from its normally open position to a closed position at which to pinch shut the reservoir inlet hose and block the flow of compressed gas from the external supply to the reservoir. The actuation finger that is also carried by the squeeze handle is moved towards and into contact with the teeth of the ratchet wheel, whereby to cause the ratchet wheel to rotate. A rotation of the ratchet wheel causes a corresponding rotation of the medication carousel within the carousel cover so that a single medication-filled chamber is axially aligned with the outlet nozzle tube of the dispenser. At the same time, the gas outlet pinch valve is moved from its normally closed position to an open position at which the previously-pinched gas outlet hose is now opened. Accordingly, a continuous fluid path is established from the gas reservoir to the outlet nozzle tube by way of the gas outlet hose, the horizontal and vertical channels of the carousel back cap, the inlet gas holes through the pair of inside sealing gaskets, the particular medication-filled chamber of the carousel, and the outlet gas holes through the pair of outside sealing gaskets. In this case, the powdered medication from the particular chamber of the carousel is entrained by a blast of gas under pressure for delivery to the patient.

By way of a further option, the handling and activation of the biomedical haemostatic powder dispenser may be facilitated by the addition of a grip to be held within the hand of the user. An activation trigger is pivotally coupled to the grip and rotatable relative to the squeeze handle of the powder dispenser. When a squeezing force is applied by the user, the activation trigger is rotated towards the squeeze handle, whereby to depress and rotate the handle. The powder dispenser is thusly activated so that a dose of powdered medication is entrained for delivery to the patient.

BRIEF DESCRIPTION OF THE DRAWINGS

FIG. 1 is perspective view of a biomedical haemostatic powder dispenser according to a preferred embodiment of the present invention;

FIG. 2 is an exploded view of the powder dispenser shown in FIG. 1;

FIG. 3 is a front view of the powder dispenser shown in FIG. 1;

FIG. 4 is a cross-section of the powder dispenser taken along lines 4-4 of FIG. 3 showing the dispenser in an at-rest condition;

FIG. 10 is a partial cross-section perspective view of an embodiment of the powder dispenser with a pressure relief valve;

FIG. 11 is an exploded view of the reservoir and pressure relief valve of the embodiment of FIG. 10;

FIG. 12 is another partial cross-section perspective view of the powder dispenser of FIG. 10;

FIG. 13 is an exploded view of the pressure relief valve illustrated in A in FIG. 12;

DETAILED DESCRIPTION OF THE INVENTION

Figure 1:
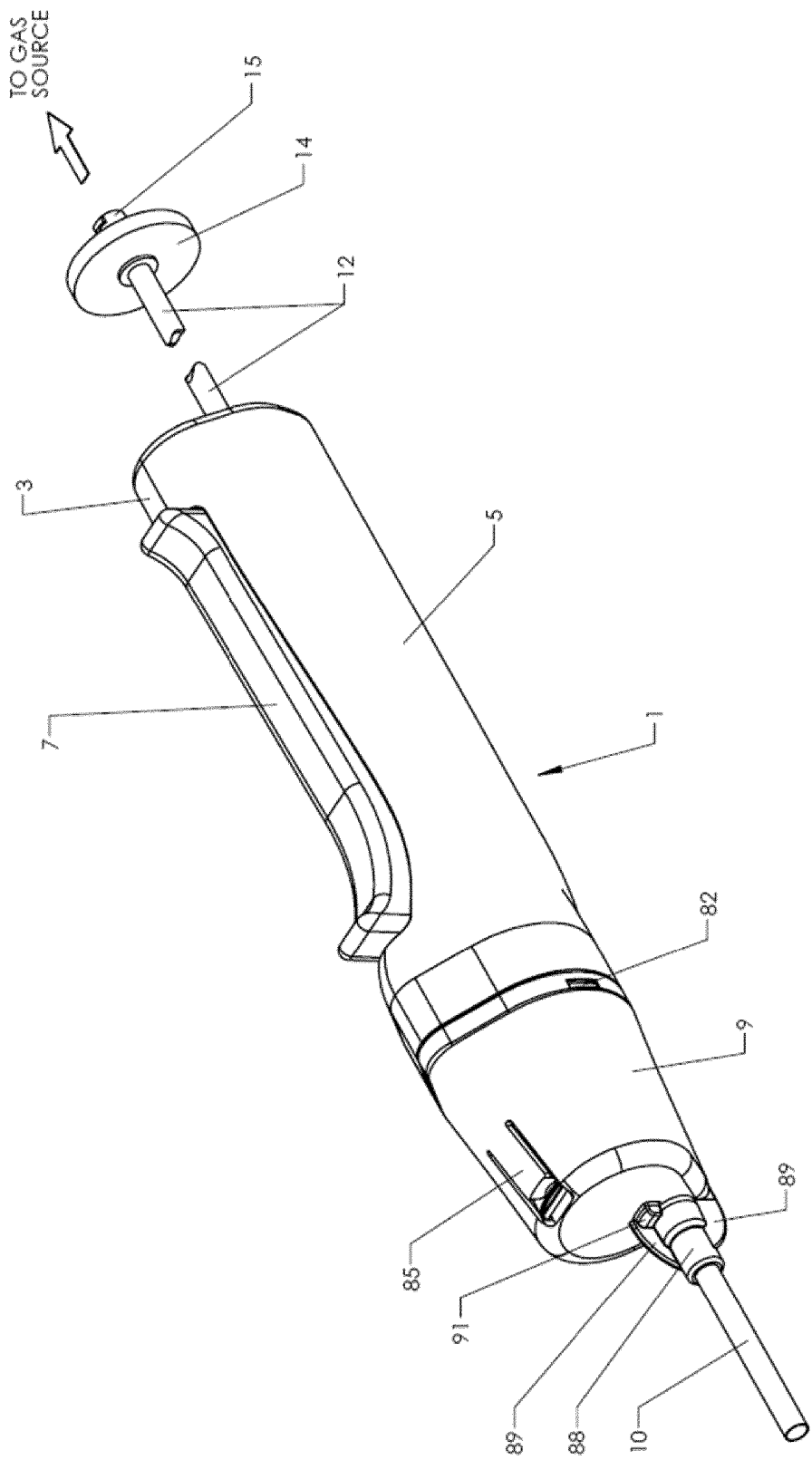

FIGS. 1 and 2 of the drawings show the biomedical haemostatic powder dispenser 1 of this invention according to a preferred embodiment in an assembled, ready-to-use configuration. As will be explained in greater detail hereinafter, the haemostatic powder dispenser 1 is adapted to deliver to a patient a precise dose of powdered medication that is entrained in a stream of air or any other suitable gas. By way of example only, the haemostatic powder dispenser 1 has particular application for delivering the powdered medication to a wound site to suppress bleeding. The powder dispenser 1 includes a pair of opposing handle shells 3 and 5 that are connected to one another by means of fasteners received through a pair of locking posts 6 that extend between the shells. A squeeze handle 7 is supported for reciprocal movement between the shells 3 and 5. As will also be explained, with the powder dispenser 1 held in the user's hand, the squeeze handle 7 can be manually depressed (i.e., squeezed) and rotated inwardly of the handle shells 3 and 5 to initiate the process by which a predictable blast of gas under pressure and the precise dose of powdered medication are mixed together and exhausted from the dispenser to the patient. Fluidizing the powdered medication in this manner will enable an accurate and complete delivery of the medication to the tissue (e.g., wound) site.

A carousel cover 9 is located between first ends of the opposing handle shells 3 and 5 and an outlet nozzle tube 10. Individual doses of powdered medication to be discharged one at a time from the dispenser 1 are stored in a soon-to-be described medication carousel 22 that is surrounded by the carousel cover 9. A gas inlet tube 12 is coupled to an inlet fitting 32 received through an entrance opening 13 formed in the opposite ends of the opposing handle shells 3 and 5.

The gas inlet tube 12 may typically be three to five meters long and runs outside the handle shells 3 and 5. An inlet filter 14 is located between the gas inlet tube 12 and a pressure regulator coupler 15. An external source of compressed gas (e.g., air, carbon dioxide or any other suitable non-toxic gas) is connected to the gas inlet tube 12 by way of a pressure regulator (not shown), in particular a gas inlet valve (not shown), more particularly an open gas inlet valve which may also be called a gas supply or gas shutoff valve (not shown), to be attached to the pressure regulator coupler 15. A regulated and filtered supply of compressed gas can be applied from the external gas source to the haemostatic powder dispenser 1 via the gas inlet tube 12. Therefore, when the squeeze handle 7 is depressed by the user, a single dose of powdered medication that is stored in the powder storage, such as the medication filled chamber 23 of the medication carousel, 22 within the carousel cover 9 will be fluidized and dispensed in a stream of gas under pressure to the patient via the outlet nozzle tube 10 in a manner that will now be disclosed.

Referring concurrently in this regard to FIGS. 2-5 of the drawings, details are now provided of the biomedical haemostatic powder dispenser 1 of FIG. 1 and the means by which a repeatable volume of gas under pressure is supplied to and mixed with a single dose of powdered medication to be blown from the dispenser and delivered to the patient. The squeeze handle 7 to be squeezed and depressed by the user relative to the opposing handle shells 3 and 5 is rotatable inwardly of the shells through adjacent openings 16 and 17 formed therein. The squeeze handle 7 has a ratchet actuator 18 at a first end thereof. Depending downwardly through the shells 3 and 5 from the ratchet actuator 18 is an actuator finger 20 (best shown in FIG. 2) which controls the rotation of a multi-dose medication carousel 22 so that a single dose of powdered medication stored within the carousel is positioned for fluidization.

Projecting downwardly and inwardly of the shells 3 and 5 from the opposite end of the squeeze handle 7 is a normally-open inlet pinch valve 24,25. This pinch valve 24,25 may comprise a movable part 24 and a stationary part 25. In particular the movable part 24 is integral and moves with the activation handle 7 and the stationary part 25 is integral with the shell 3. Also projecting from the opposite end of handle 7 and lying inside handle shells 3 and 5 is a handle hinge pin 26. The pinch valve 24,25 communicates with and controls the gas flow through a reservoir inlet hose 28. The handle hinge pin 26 is pivotally received within a cylindrical pivot post 29 that projects inwardly from the opposing shells 3 and 5. Thus, when the handle 7 is squeezed and depressed to activate the powder dispenser 1, the handle 7 will rotate at the handle hinge pin 26 within pivot post 29 so that the actuator finger 20 carried by the handle will be correspondingly moved to control the rotation of the medication carousel 22.

A hollow (e.g., cylindrical) sealed gas reservoir 30 is surrounded by and cradled between the handle shells 3 and 5. One end of the reservoir inlet hose 28 is coupled to the back end of reservoir 30 within the shells 3 and 5. The opposite end of the reservoir inlet hose 28 is coupled to the gas inlet tube 12 at the aforementioned inlet fitting 32 through the handle shells 3 and 5. Therefore, an inlet gas flow path is established from the external source of compressed gas to the gas reservoir 30 via the gas inlet tube 12 and the reservoir inlet hose 28. The flow of gas to reservoir 30 through the reservoir inlet hose 28 is controlled by the inlet pinch valve 24,25 in response to the user depressing the squeeze handle 7.

The front end of the gas reservoir 30 is closed by a reservoir cap 34. A duckbill valve (i.e., a one-way check valve) 36 communicates with the gas reservoir 30 through the reservoir cap 34. The duckbill valve 36 is surrounded by a combination valve and tube fitting 38 that is mounted in the cap 34 at the front end of the gas reservoir 30. One end of an elastic gas outlet hose 40 is coupled to the valve and tube fitting 38 so as to communicate with the gas reservoir 30 by way of the duckbill valve 36. The opposite end of the gas outlet hose 40 is coupled to a carousel back cap (designated 50 and best shown in FIG. 5).

The gas outlet hose 40 coupled to the gas reservoir 30 is received through a normally closed gas outlet pinch valve 42. The operation of pinch valve 42 (best shown in FIGS. 7 and 8) is controlled by a (e.g., coil) spring 44 that surrounds the valve 42 and engages the inside of the handle shells 3 and 5. The spring 44 is either relaxed or compressed depending upon whether the squeeze handle 7 is depressed by the user. In the case when the handle 7 is not depressed during the at-rest condition of the powder dispenser 1 (best shown in FIG. 4), the spring 44 is relaxed and expanded, and the gas outlet pinch valve 42 is urged by the spring 44 to clamp the gas outlet hose 40 so as to prevent the flow of gas between the reservoir 30 and the carousel back cap 50.

The medication carousel 22 which is surrounded by the carousel cover 9 includes a plurality of (e.g., sixteen) chambers 23, each of which being filled with a measured dose of powdered medication ready to be delivered to the patient by a blast of pressurized gas from the gas reservoir 30. As earlier explained, the carousel 22 is rotated as the squeeze handle 7 is depressed by the user, whereby a single chamber 23 from the carousel is positioned so that the dose of powdered medication stored therein can be entrained and exhausted by the gas blast.

To this end, the actuator finger 20 which depends downwardly from the ratchet actuator 18 at one end of the squeeze handle 7 of the powder dispenser 1 is interfaced with teeth 49 around a ratchet wheel 48. The ratchet wheel 48 is connected to the carousel 22 by a shaft 52 that runs through a center hole 54 in the carousel back cover 50. The shaft 52 includes a pair of flexible locking fingers (designated 53 and best shown in FIG. 5) projecting therefrom to be snapped into locking engagement within the medication carousel 22. Whenever the squeeze handle 7 is depressed and rotated inwardly of the handle shells 3 and 5 during the activated condition of the powder dispenser 1 (best shown in FIG. 6), the actuator finger 20 that is carried by the squeeze handle 7 applies a pushing force to the teeth 49 of the ratchet wheel 48, whereby to cause the ratchet wheel to rotate. The rotation of ratchet wheel 48 is transferred to the carousel 22 by way of the shaft 52 to cause a corresponding rotation of the carousel within the carousel cover 9.

Figure 4:
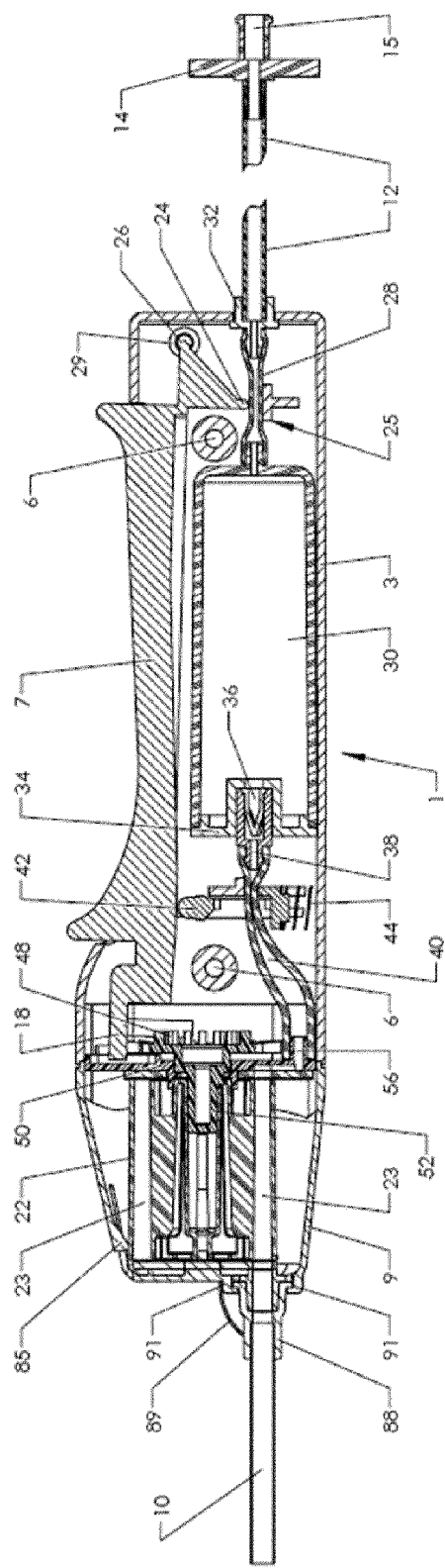
Figure 3:
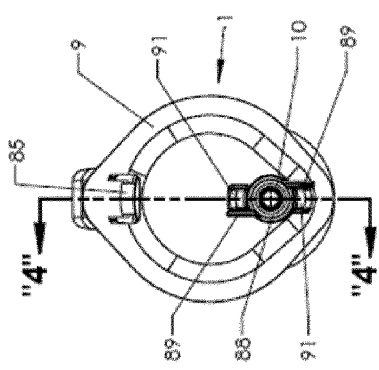
Figure 5:
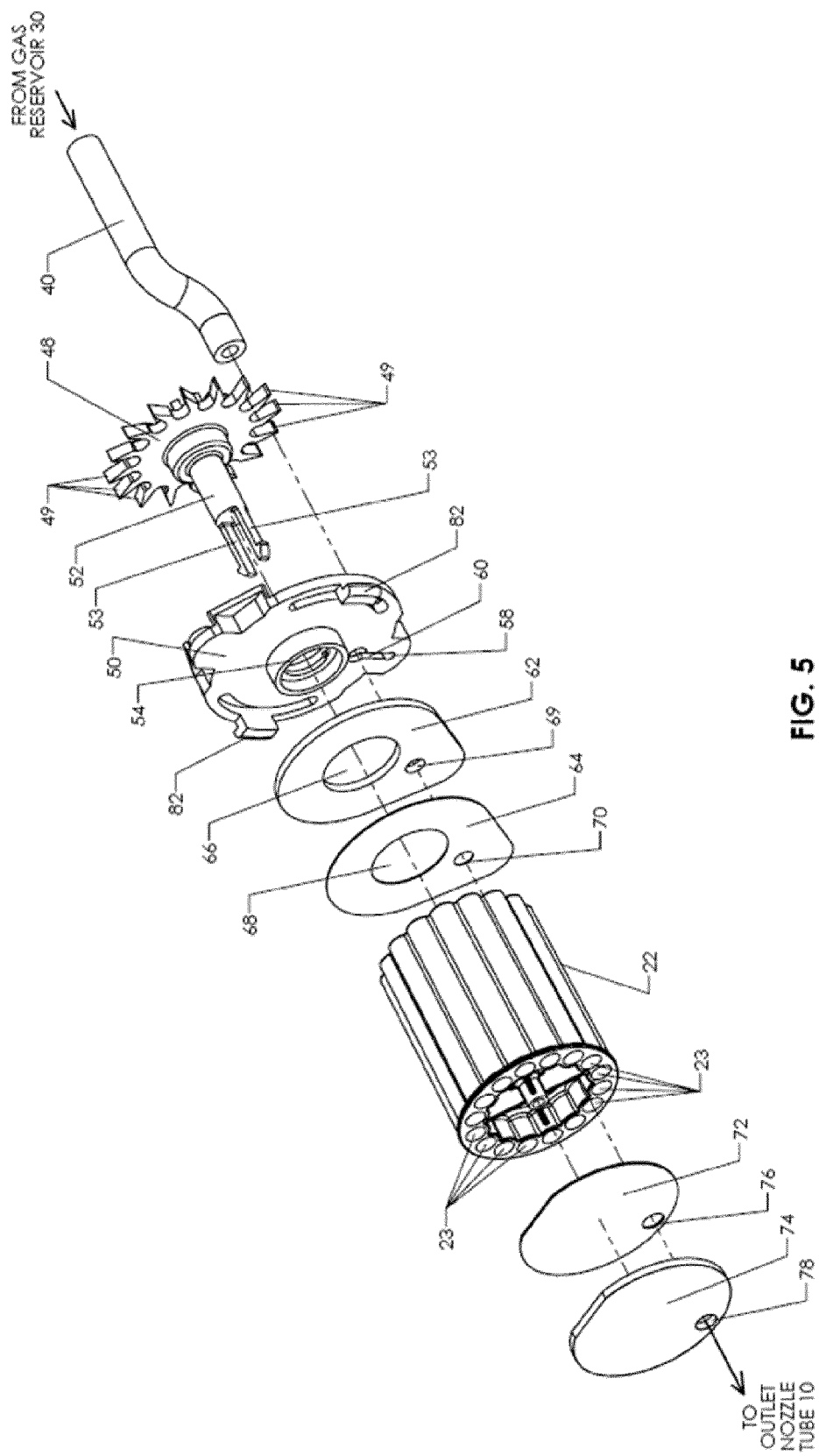
FIG. 5 illustrates a continuous fluid path through the powder dispenser when the dispenser is in an activated condition to deliver a dose of powdered medication to a user.

Referring particularly to FIG. 5 of the drawings, the gas outlet hose 40 which communicates with the gas reservoir 30 by way of the duckbill (check) valve 36 is shown aligned with the carousel back cap 50. In particular, the gas outlet hose 40 is connected to a gas coupler 56 (best shown in FIG. 4) at the rear of the carousel back cap 50. The gas coupler 56 of back cap 50 lies in fluid communication with successive horizontal (i.e., inward) and vertical (i.e., upward) channels 58 and 60 that run through the carousel back cap 50. The channels 58 and 60 of the back cap 50 apply the gas carried by the gas outlet hose 40 to a particular one of the medication-filled chambers 23 of the carousel 22 depending upon the position to which the carousel has been rotated when the squeeze handle 7 is depressed. Thus, it may be appreciated that the gas which flows from outlet hose 40 to carousel 22 travels in two different directions through the horizontal and vertical channels 58 and 60 of the carousel back cap 50. The bi-directional gas flow path through the back cap 50 is desirable to accommodate a large diameter ratchet wheel 48 and the ability to accurately index the carousel 22.

The front of the carousel back cover 50 is covered by a pair of sliding inside gaskets 62 and 64 (best shown in FIG. 5) that are disposed face-to-face one another. The inside gaskets 62 and 64 seal the back of the carousel 22 and the back ends of the medication-filled chambers 23 thereof. A first 62 of the pair of inside gaskets 62 and 64 that lies against the carousel back cover 50 is preferably manufactured from a resilient material such as foam. The second 64 of the inside gaskets that lies over the first gasket 62 and against the back of the carousel 22 is preferably manufactured from a low-friction material such as that known as Teflon. Each of the pair of inside gaskets 62 and 64 has a central opening 66 and 68 formed therethrough to accommodate the shaft 52 and the locking fingers 53 which extend from the ratchet wheel 48 to the carousel 22 in order to impart a rotation to the carousel relative to the back cap 50. Each of the pair of sliding inside gaskets 62 and 64 also has an inlet gas hole 69 and 70 extending therethrough. The inlet gas holes 69 and 70 of the inside gaskets 62 and 64 are axially aligned with each other, with the top of the vertical (i.e., upward) channel 60 of the carousel back cap 50, and with a particular one of the medication-filled chambers 23 of the carousel 22 to be accessed depending upon the position to which the carousel has been rotated.

A pair of sliding outside gaskets 72 and 74 are disposed face-to-face one another so as to seal the front of the carousel 22 and close the front ends of the medication-filled chambers 23. A first 72 of the pair of outside gaskets 72 and 74 that lies against the front of the carousel 22 is preferably manufactured from Teflon. The second 74 of the outside gaskets that lies over the first gasket 72 and presses against the interior of the carousel cover 9 within which the carousel 22 and the pairs of inside 62 and 64 and outside 72 and 74 gaskets are housed is preferably manufactured from foam. Each of the pair of sliding outside gaskets 72 and 74 has an outlet gas hole 76 and 78 extending therethrough. The outlet gas holes 76 and 78 of the outside gaskets 72 and 74 are axially-aligned with each other, with the particular one of the medication-filled chambers 23 of the carousel 22 to be accessed, and with the outlet nozzle tube 10 that is coupled to the carousel cover 9.

The carousel back cap 50 has a pair of flexible snaps 82 located at opposite sides thereof. The medication carousel 22 and the pairs of sliding inside and outside gaskets 62, 64 and 72, 74 which seal the front and back of the carousel are located inwardly of and surrounded by the carousel cover 9. The carousel back cap 50 is mounted across the back of the carousel cover 9 so that the carousel 22 is rotatable inside the cover 9 and relative to the carousel back cover 50 in response to a depression of the squeeze handle 7. The carousel back cap 50 is attached to the carousel cover 9 when the flexible snaps 82 of the back cap 50 are snapped into locking engagement with respective locking slots 84 that are formed in the cover 9 (best shown in FIG. 2).

The ratchet wheel 48 is located behind the carousel cover 9 so as to lie below the actuation finger 20 that is pushed towards the teeth 49 of the ratchet wheel 48 in response to a depression of the squeeze handle 7 to cause the wheel to rotate when the powder dispenser 1 is activated. Because the ratchet wheel 48 is connected to the carousel 22 by shaft 52, each depression of the squeeze handle 7 causes a predetermined rotation of the carousel 22 so that successive ones of the plurality of powdered medication-filled chambers 23 of the carousel 22 are moved into a continuous fluid path running between the gas outlet hose 40 and the outlet nozzle tube 10 and including the horizontal and vertical channels 58 and 60 of the carousel back cap 50, the inlet holes 69 and 70 through the pair of inside gaskets 62 and 64, the particular powder-filled carousel chamber 23 to be accessed, and the gas outlet holes 76 and 78 through the pair of outlet gaskets 72 and 74.

The carousel cover 9 includes a flexible indexing tab 85 having a spring memory and projecting inwardly into engagement with the carousel 22 at the intersection between adjacent chambers 23 thereof. The indexing tab 85 indexes the carousel 22 during its rotation inside the carousel cover 9 whenever the squeeze handle 7 is depressed so that only a single powder-filled chamber 23 is moved into the aforementioned fluid path between outlet hose 40 and outlet nozzle tube 10. The carousel cover 9 also includes a coupler 86 which projects from the front thereof opposite the back cap 50. A nozzle hub 88 to which the outlet nozzle tube 10 is attached is rotated into detachable connection with the coupler 86. That is, a pair of finger wings 89 project from the nozzle hub 88 to receive a rotational force thereagainst by which locking tabs 90 that are carried by hub 88 are rotated below and into locking engagement with corresponding locking tab receivers 91 on the carousel cover 9. The outlet nozzle tube 10 is bonded to the detachable nozzle hub 88 so that different hubs having different tube lengths can be attached to the coupler to communicate with the particular powder-filled chamber 23 of the medication carousel 22 that is rotated into the continuous fluid path which extends between the gas outlet hose 40 and the outlet nozzle tube 10.

FIG. 4 shows the biomedical haemostatic powder dispenser 1 in an at-rest condition. That is to say, the gas reservoir 30 is filled with a known volume (e.g., about 10 cc) of compressed gas supplied thereto from the external gas source via the gas inlet tube 12 and the reservoir inlet hose 28. No squeezing force is being applied to the squeeze handle 7 by the user. Therefore, the normally-open inlet pinch valve 24,25 which depends from and is movable with the squeeze handle 7 remains opened such that the reservoir inlet hose 28 is not constricted and blocked at which time the reservoir 30 is filled. At the same time, the normally-closed gas outlet pinch valve 42 is biased by its spring 44 so as to remain closed and crimp shut the elastic gas outlet hose 40 from gas reservoir 30. In this case, the flow of gas from the reservoir 30 to the carousel back cap 50 by way of the gas outlet hose 40 is blocked. Accordingly, with the powder dispenser 1 at rest, no gas will be supplied from the gas reservoir 30 to any of the medicated powder-filled chambers 23 of the carousel 22.

Figure 6:
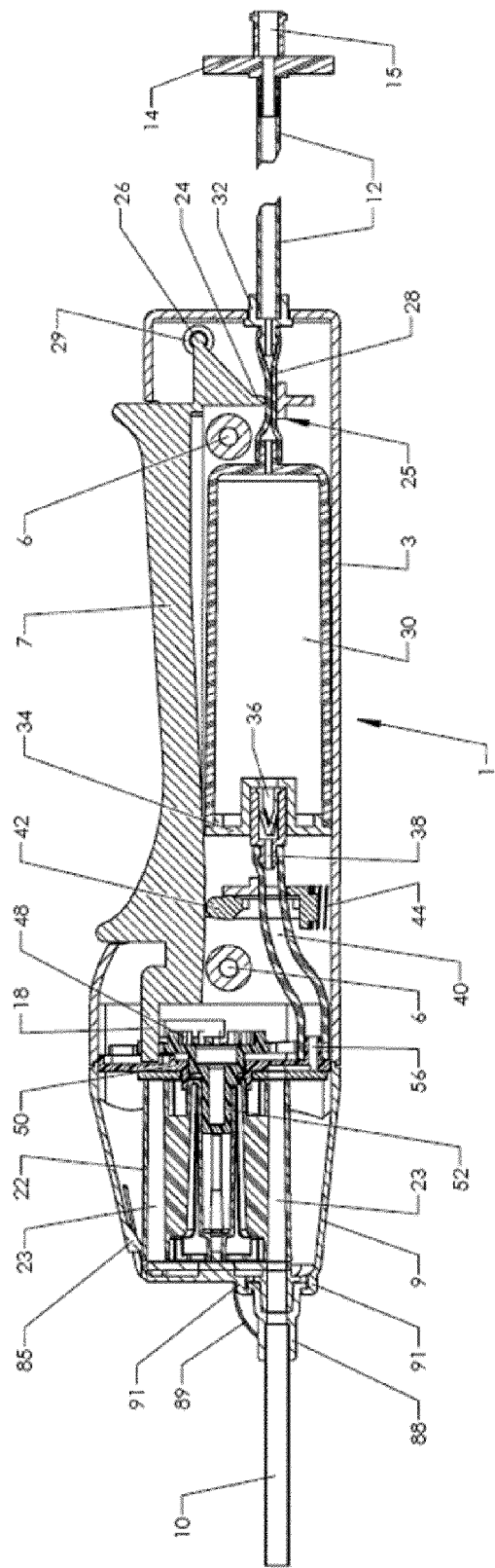
FIG. 6 is a cross-section of the powder dispenser in an activated condition.

Turning now to FIG. 6 of the drawings, the biomedical haemostatic powder dispenser 1 is shown in the activated condition during which a pre-measured dose of powdered medication is delivered from the medication carousel 22 to the patient. To activate the powder dispenser 1, the user (e.g., a healthcare worker) applies a squeezing force to depress the squeeze handle 7 by which the handle rotates at handle hinge pin 26 so as to move inwardly of the handle shells 3 and 5. The inward movement of squeeze handle 7 causes the normally-opened inlet pinch valve 24,25 that is carried by the handle to correspondingly move towards and into contact with the reservoir inlet hose 28. The pinch valve 24,25 is now closed so that inlet hose 28 is pinched shut and constricted, whereby communication between the external gas source and the gas reservoir 30 is blocked.

At the same time, the depression and rotation of the squeeze handle 7 during the activated condition of the powder dispenser 1 pushes the actuator finger 20 that is carried by the handle 7 towards and into contact with the teeth 49 of the ratchet wheel 48, whereby to cause the wheel to rotate. The rotation of ratchet wheel 48 is transferred via the shaft 52 to the medication carousel 22 so that the carousel rotates within the carousel cover 9 relative to the carousel back cap 50 and the pairs of sliding inside and outside gaskets 62, 64 and 72, 74. Accordingly, the carousel 22 is rotated so that a single powder-filled chamber 23 is moved into the fluid path between the gas outlet hose 40 from the gas reservoir 30 and the outlet nozzle tube 10 while a spent chamber from which powder was previously dispensed is moved out of the fluid path.

What is more, the depression of the squeeze handle 7 during the activated condition of the powder dispenser 1 also moves the gas outlet pinch valve 42 from its normally closed position to an opened position. Accordingly, the former constriction of the gas outlet hose 40 during the at-rest condition is removed, and a gas flow path is now opened through the outlet hose 40 until the squeezing force applied to the squeeze handle 7 is terminated. By virtue of the foregoing, the aforementioned continuous fluid path is established along which gas is blown under pressure through the powder dispenser 1 from the gas reservoir 30 to the outlet nozzle tube 10 by way of the duckbill valve 36 (which prevents backflow from the medication carousel 22 to the reservoir), the gas outlet hose 40, the horizontal and vertical channels 58 and 60 (of FIG. 5) of the carousel back cap 50, the inlet gas holes 69 and 70 through the pair of inside gaskets 62 and 64, the particular powder-filled chamber 23 of carousel 22 to be accessed, and the outlet gas holes 76 and 78 of the pair of outside gaskets.

The measured dose of powdered medication that is stored within the particular medication chamber 23 is mixed with the gas that is exhausted from the gas reservoir 30. Therefore, the powdered medication is entrained for delivery by a blast of gas to the patient via the outlet nozzle tube 10 of the powder dispenser 1.

Following the delivery of the medication to the patient, the squeeze handle 7 is released and the biomedical haemostatic powder dispenser 1 automatically returns to its at-rest condition. In this case, the inlet pinch valve 24 moves upwardly with the handle 7 and out of contact with the reservoir inlet hose 28, whereby the hose 28 is no longer pinched shut and the gas reservoir 30 is refilled with gas under pressure. The gas outlet pinch valve 42 is urged by the spring 44 to return to its normally closed at-rest position to block the gas-filled reservoir 30 from the medication carousel 22 until the squeeze handle 7 is once again squeezed so that a new measured dose of powdered medication can be delivered in the manner previously disclosed.

Figure 7:
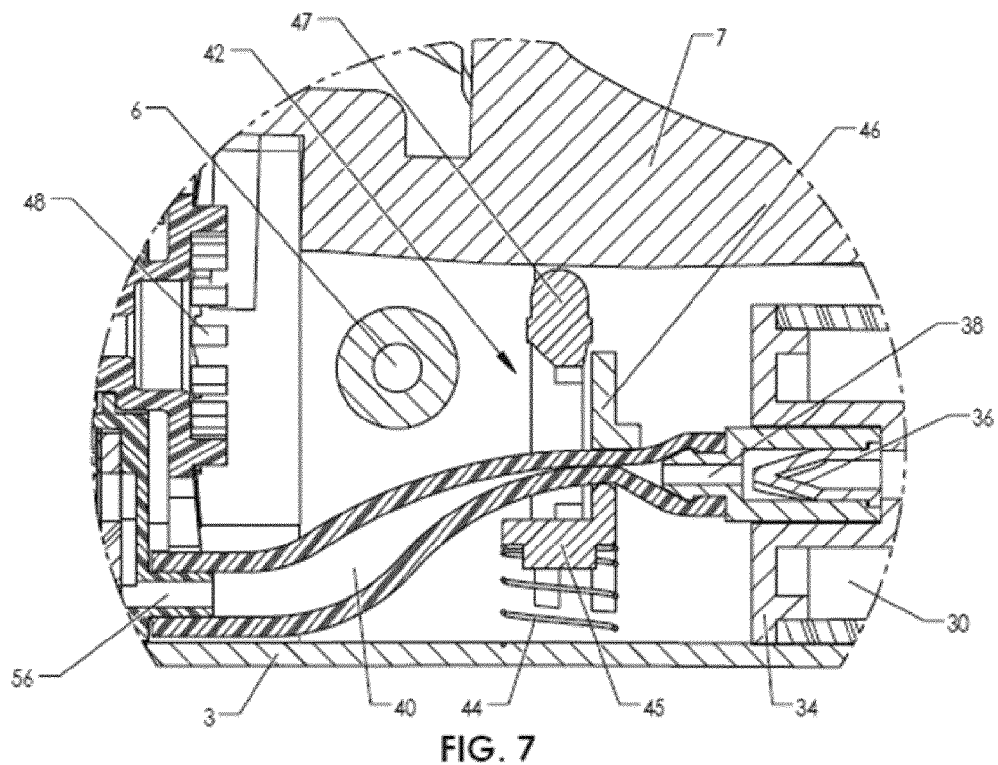
FIG. 7 shows a spring-biased, normally-closed gas outlet pinch valve of the powder dispenser in a closed position.
Figure 8:
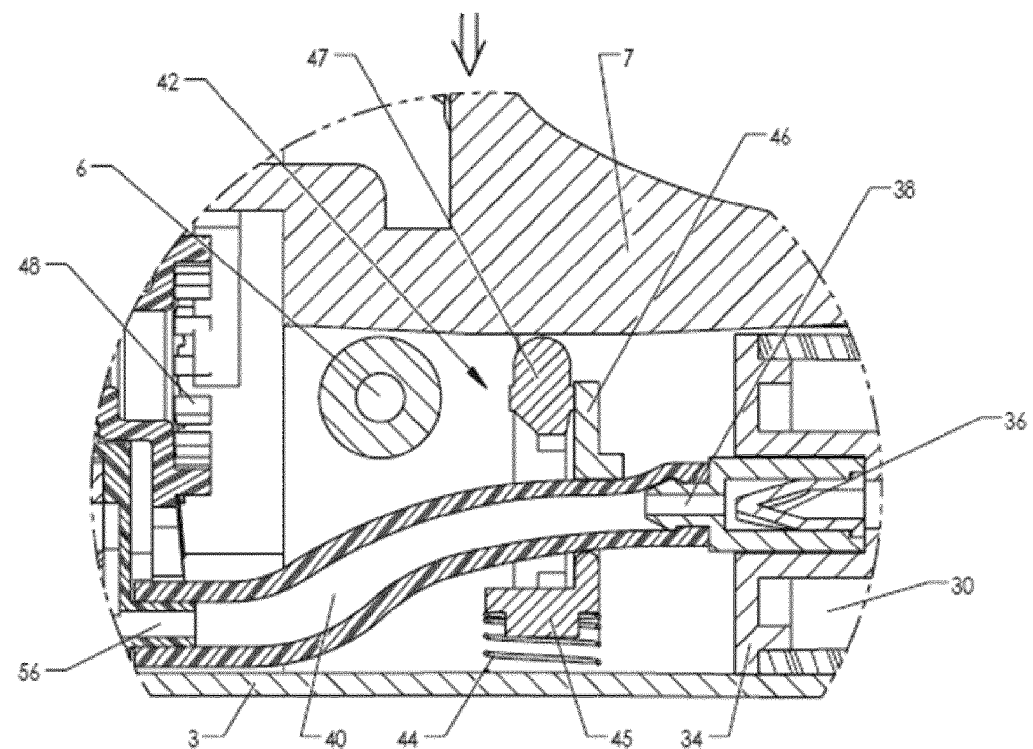
FIG. 8 shows the gas outlet pinch valve of FIG. 7 in an open position.

Referring in this regard to FIGS. 7 and 8 of the drawings, details are provided of the normally-closed spring-biased gas outlet pinch valve 42 that controls the flow of gas through the elastic gas outlet hose 40 between the gas reservoir 30 and the particular powdered medication-filled chamber 23 to be accessed from the medication carousel 22. FIG. 7 shows the outlet pinch valve 42 in its normally-closed position so that the gas outlet hose 40 is pinched shut when the biomedical haemostatic powder dispenser 1 is in its at-rest condition of FIG. 4. The pinch valve 42 includes a movable clamp 45 and a stationary anvil 46 that are spaced from one another. The gas outlet hose 40 runs between the clamp 45 and the anvil 46. The clamp 45 of pinch valve 42 is surrounded by the (coil) spring 44 which abuts the handle shells (only one of which 3 being visible). The movable clamp 45 engages the squeeze handle 7 by way of a force-transmitting member 47 that is responsive to a depression and rotation of the handle 7. The force transmitting member 47 is attached to and travels with the clamp 45 of pinch valve 42.

With the powder dispenser 1 at rest, no squeezing force is applied by the user and the squeeze handle 7 remains stationary. The spring 44 which surrounds the clamp 45 of pinch valve 42 is relaxed and expanded whereby to urge the movable clamp 45 upwardly towards the stationary anvil 46. Thus, the gas outlet pinch valve 42 is closed and the gas outlet hose 40 is pinched shut between the clamp 45 and the anvil 46. In this case, gas flow through hose 40 is blocked.

FIG. 8 shows the powder dispenser 1 in the activated condition of FIG. 6 when a squeezing force (represented by the direction of the reference arrow) is applied to the squeeze handle 7 by the hand of the user. Accordingly, the handle 7 is depressed and rotated inwardly of the handle shells (e.g., 3). A depression of the handle 7 is transmitted to the force-transmitting member 47 of the pinch valve 42 so as to force the clamp 45 of pinch valve 42 to move and separate from the stationary anvil 46 so that the spring 44 is compressed. The elasticity of the gas outlet hose 40 enables the hose to recover and open between the clamp 45 and the anvil 46. The normally-closed gas outlet pinch valve 42 is now opened so that the outlet hose 40 is no longer pinched shut. In this case, a blast of gas from the reservoir 30 can be delivered to the medication-filled chamber 23.

At the conclusion of activated condition of the medication dispenser, the squeezing force applied to squeeze handle 7 is terminated. The compressed spring 44 is allowed to expand, and the pinch valve 42 is once again closed so as to urge the handle 7 to rotate upwardly to its at-rest position shown in FIG. 4.

Figure 9:
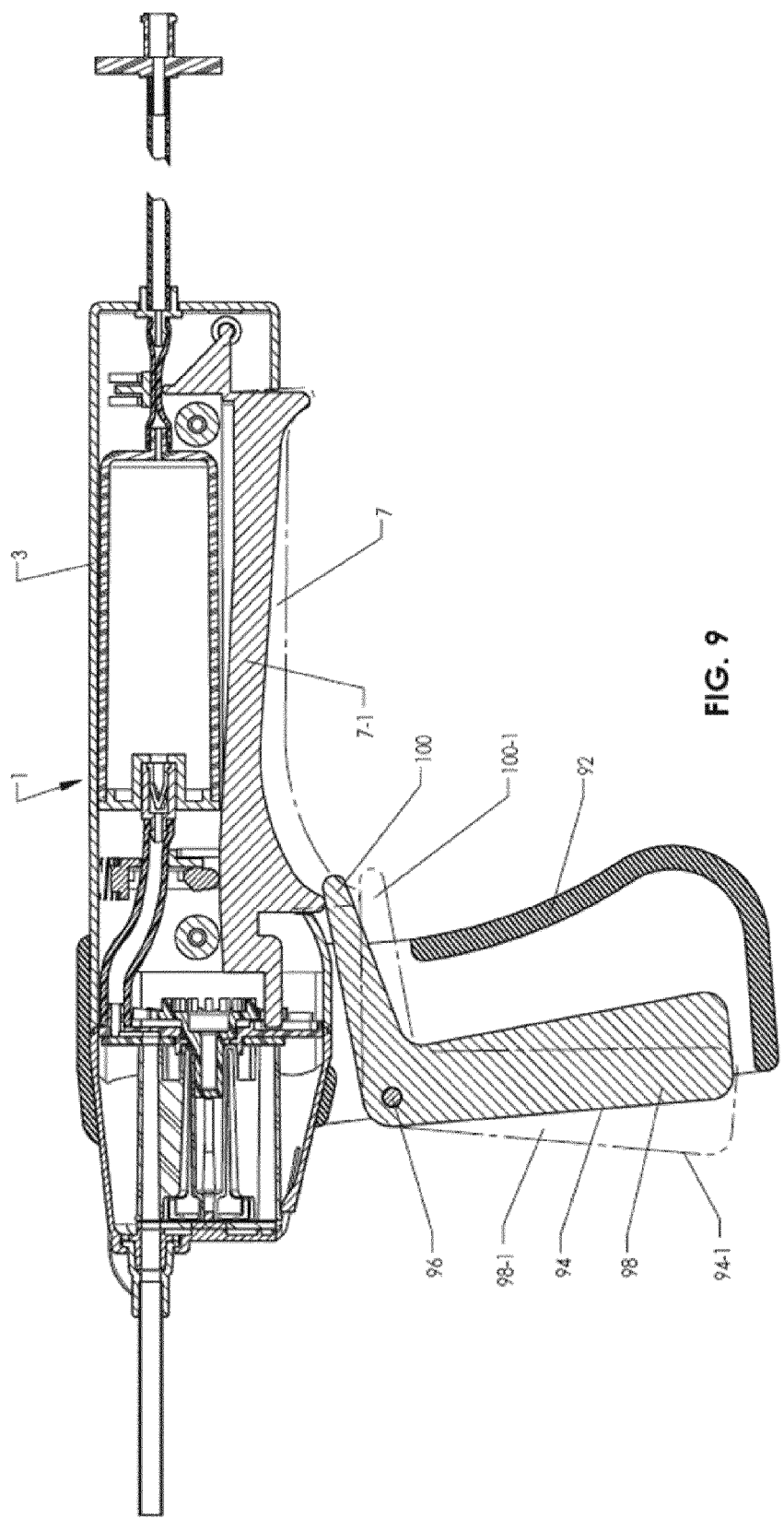
FIG. 9 shows the powder dispenser including an optional grip having a rotatable activation trigger by which the dispenser is carried and activated.
Figure 14:
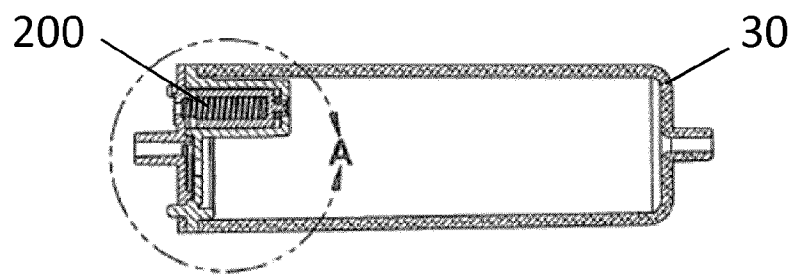
FIG. 14 is a cross-section view of the reservoir and pressure relief valve of the embodiment of FIG. 10

Turning now to FIG. 9 of the drawings, in order to facilitate the activation of the biomedical haemostatic powder dispenser 1 of FIGS. 1-8, an open-ended, elongated grip 92 is connected to the dispenser below the handle shells (only one of which 3 being visible). The grip 92 can be grasped in the hand of the user so that dispenser 1 can be easily transported and positioned (including laparoscopically) relative to the tissue area of the patient to be treated.

An actuation trigger 94 is surrounded by the grip 92 and adapted to be moved (i.e., rotated) inwardly through the open end thereof. To this end, the trigger 94 is pivotally connected to the grip 92 at a pivot pin 96 so that the trigger is rotatable relative to the squeeze handle 7 from a relaxed position (designated 94-1 and shown in phantom lines) when the powder dispenser 1 is in the at-rest condition of FIG. 4 and none of the powdered medication is being delivered to the patient to a medication delivery position when the powder dispenser 1 is in the activated condition of FIG. 6 and a dose of powdered medication is entrained for delivery to the patient.

In this regard, the trigger 94 includes a force-responsive end 98 and a handle depression end 100. Prior to activation of the dispenser 1, no gripping force is applied by the user to the force-responsive end, and the trigger 94-1 is relaxed. In this case, the force-responsive end 100-1 of the trigger 94-1 applies no pushing force to the squeeze handle 7.

In order to activate the dispenser 1 and dispense a dose of powdered medication therefrom, the user applies a gripping force to the force-responsive end 98-1 of the actuation trigger 94-1, whereby to cause the trigger to rotate in a first direction at pivot pin 96 from its relaxed position to its medication delivery position. The handle depression end 100 of trigger 94 is correspondingly pushed against the squeeze handle 7-1, whereby to cause the handle to rotate as previously explained and move inwardly of the handle shells (e.g., 3) of the dispenser 1. With the handle 7-1 depressed, the powder dispenser 1 is now in the activated condition in the manner disclosed when referring to FIG. 6 so as to open a continuous fluid path from the gas reservoir 30 to the particular chamber 23 of the carousel 22 to be accessed so that the medicated contents thereof may be delivered to the patient via the outlet nozzle tube 10.

When the user releases the gripping force on the force-responsive end 98, the actuation trigger 94 automatically rotates in an opposite direction at the pivot 96. That is, as the spring 44 of the gas outlet pinch valve 42 expands at the conclusion of the activated condition of the powder dispenser 1, the trigger 94 is urged by the squeeze handle 7 to return to its relaxed position, and the dispenser 1 is once more in the at-rest condition to await a new activation.

In a particular embodiment, the proposed biomedical hemostatic powder dispenser includes a number of elements to avoid exposing the patient to an excessively pressurized pulse of gas. Indeed, should an operator misadjust or bypass the gas pressure regulator provided on the gas supply and connected to the powder medication dispenser by the pressure regulator coupler 15, it is preferable to have a back-up pressure limiting capability. To this end, the dispenser may comprise a pressure relief valve 200 arranged on the pressurized gas reservoir 30. The pressure relief valve 200 is adapted to allow gas to escape from the reservoir 30 when the internal pressure exceeds a set limit.

The elements of the pressure relief valve 200 are shown in FIGS. 10 to 16. The reservoir 30 is fitted with a reservoir cap 34a that substantially closes the reservoir 30 while providing two outlet paths for the pressurized gas in the reservoir 30 as shown in FIG. 11. One path P1 is routed toward the outlet nozzle 10 of the powder dispenser through the carousel 22 as previously described. The second path P2 is for the release of gas from the reservoir 30 that exceeds a set pressure limit.

Figure 15:
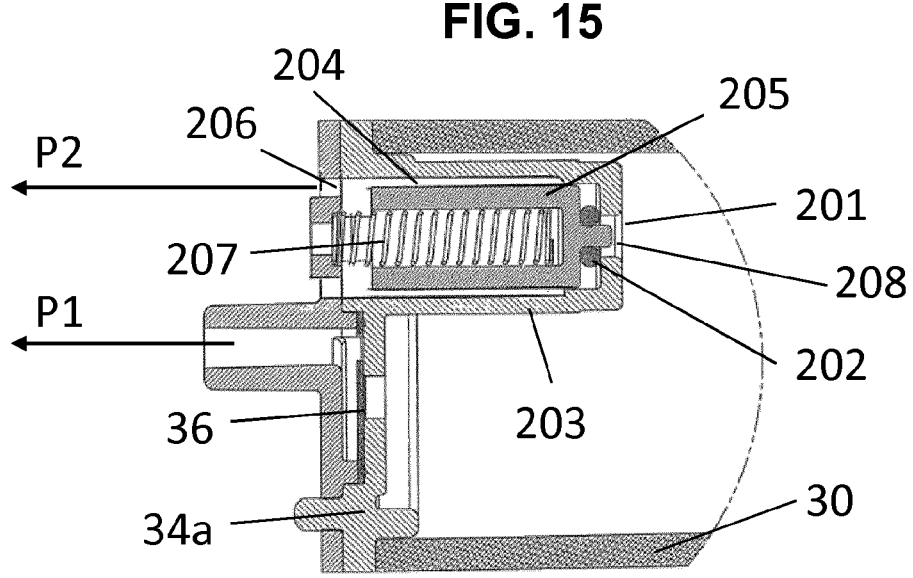
FIG. 15 is a cross-section view of the pressure relief valve of FIG. 14 in a closed position.
Figure 16:
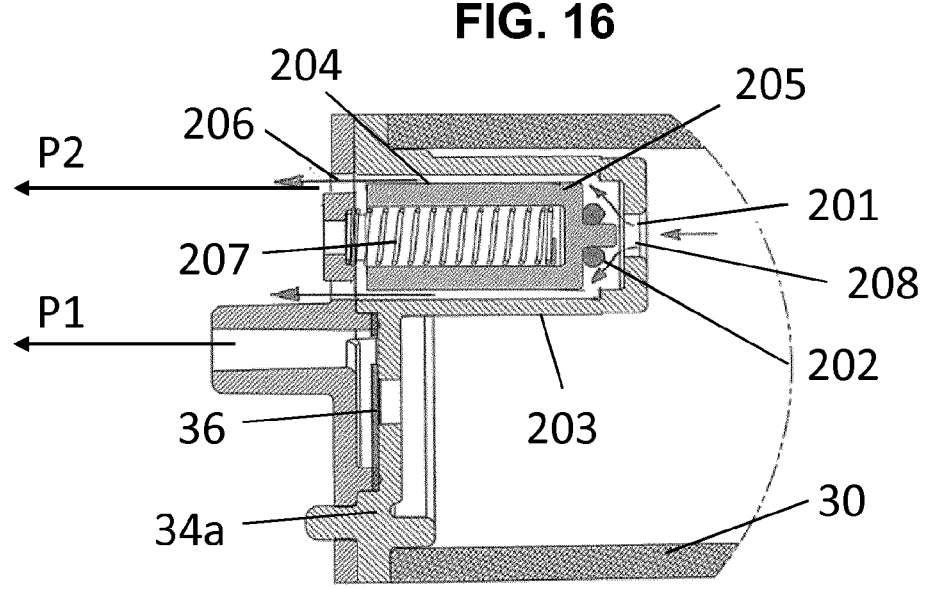
FIG. 16 is a cross-section view of the pressure relief valve of FIG. 14 in an opened position.

The second path is best shown in FIG. 16 which illustrates a path for the gas to escape, that flows from the interior of the reservoir 30 through the relief valve inlet 201, past the O-Ring 202, through the space 204 between the interior of the piston housing 203 and exterior of the pressure relief valve piston 204, and exiting through the relief valve outlet(s) 206. This second path is normally closed by means of a preload spring 207 applying force to drive the piston 205 and attached O-Ring 202 into sealing contact with the perimeter of the relief valve inlet 201. This is best shown in FIG. 15.

Should the gas pressure in the reservoir 30 exceed the set pressure threshold, then the force applied by the gas pressure on the piston 205 will exceed the spring 207 preload force and lift the piston 205 with attached O-Ring 202 away from sealing contact with the perimeter of the relief valve inlet 201. As gas escapes the reservoir 30, the pressure decreases until the preload spring 207 can return the piston 205 and O-Ring 202 into sealing contact with the relief valve inlet 201, in order to close the second path P2. The relief valve 200 can be cycled repeatedly.

The relief valve 200 may include features to improve its performance. Thus, in one embodiment, there is provided a pin 208 extending from the piston 205 onto which the O-Ring 202 is mounted. This pin 208 secures the O-ring 202 in a position centered over the perimeter of the relief valve inlet 201.

The piston housing 203 may further include alternating piston guide surfaces 209 and bypass channels 210 shown best in FIG. 13, that serve to keep the piston 205 aligned while allowing gas to escape along the sides of the piston 205.

The combined elements of the pressure relief valve 200 act to avoid exposing the patient to gas pressure beyond the preset limit controlled by the pressure relief valve.

The powder to be delivered may in particular a powder comprising, or consisting of, a pharmaceutical composition, which may have a mechanical and/or a biological effect on cells or on the organism of a subject. The powder may in particular comprise collagen.

In a specific embodiment, the powder is a haemostatic powder. This powder may comprise, or consist in:
  collagen, in particular in an amount ranging from 50 to 100% by weight compared to the total weight of the composition, and
  at least one compound chosen from:
    coagulation factors, such as thrombine, and
    osidic compounds, in particular glycosaminoglycans and/or monosaccharides.

In particular the collagen comprises fibrous and/or fibrillar collagen in an amount of at least 60% by weight, more particularly at least 70% by weight, still more particularly at least 75% by weight, or even at least 80% by weight, more particularly at least 85% by weight, still more particularly at least 90%, even more particularly at least 95%, especially at least 98% en compared to the total weight of the collagen. Following an embodiment the collagen is totally under the fibrous and/or fibrillar form.

By <<fibrous or fibrillar>> is meant collagen under fibril form, i.e. fibrillar collagen, or under fibre form, corresponding to fibrils assembly, i.e. fibrous collagen.

More precisely fibrils have a diameter ranging from 10 nm to 1 μm and fibres a diameter ranging from 1 μm to 10 μm.

Fibrous and fibrillar collagen definition may in particular correspond to the one given in <<Nature designs tough collagen: explaining the nanostructure of collagen fibrils>>, de Markus Buehler, in PNAS, 15 august 2006, vol. 103, n° 33, pp 12285-12290.

The collagen may be chosen from type I or type I and III.

The collagen may in particular be obtained from a basic extraction.

The collagen may be crosslinked, for example with Thermal Dehydratation (DHT), bridging agents, e.g. formaldehyde and/or glutaraldehyde; oxydized polysaccharides oxydés, e.g. according to the method disclosed in FR 09/5268 and/or oxydized amylopectines.

The composition may comprise an amount of collagen of at least 70% by weight, at least 75% by weight, at least 77% by weight, at least 80% by weight compared to the total weight, in particular dry weight, of the composition.

The composition may comprise an amount of collagen of at most 99% by weight, at least 96% by weight, at least 93% by weight, at least 90% by weight compared to the total weight, in particular dry weight, of the composition.

When composition does not comprise osidic compounds, but comprise at least one coagulation factor, such as thrombine, the amount of collagen may be around 99.9% by weight compared to the total weight, in particular dry weight, of the composition.

The amount of collagen may range from 70 to 99% by weight, in particular from 75 to 96% by weight, more particularly from 77 to 93% by weight, more particularly from 80 to 90% by weight compared to the total weight, in particular dry weight, of the composition.

By <<dry total weight of the composition>>, is meant the total weight of the composition without solvent, and in particular without water, thus a total weight of anhydrous composition.

The weight and the percentages of the components may correspond to the anhydrous weight of these components, and also to the corresponding percentages.

The composition may comprise at least one, in particular one coagulation factor, in particular thrombin.

It may come from animal source or from recombining source.

The amount of coagulation factor, in particular thrombin is below 0.1% by weight compared to the total weight, in particular dry weight, of the composition.

In case of thrombin the amount may range from 0.01 to 20 UI/mg, 0.05 to 10 UI/mg, 0.1 to 5 UI/mg, or 0.2 to 2 UI/mg of the composition, in particular dry composition.

The composition may comprise at least one osidic compound, in particular chosen from glycosaminoglycans, monosaccharides and their mixtures.

The composition may comprise an amount of osidic compound(s) ranging from 2 to 25% by weight, 5 to 23% by weight, 7 to 21% by weight, or 10 to 18% by weight compared to the total weight, in particular dry weight, of the composition.

The composition may present a weight ratio collagen/osidic compound(s) ranging from 2 to 50, in particular 3 to 33, more particularly 4 to 25, or 5 to 20.

The composition may comprise at least one, in particular one, glycosaminoglycan. More precisely the glycosaminoglycan does not exhibit an anti-coagulating activity.

Glycosaminoglycan may be chosen from chondroitin sulfate, dermatane sulfate and hyaluronic acid, in particular chondroitin sulfate.

Glycosaminoglycans may improve the absorption speed of the blood by the composition. It may speed the contact between blood and haemostatic components, in particular collagen, with thrombin.

Composition may comprise an amount of glycosaminoglycan ranging from 2 to 25% by weight, from 3 to 20% by weight, from 4 to 15% by weight, or from 5 to 12.5% by weight compared to the total weight, in particular dry weight, of the composition.

Composition may have a weight ratio collagen/glycosaminoglycan from 2.5 to 50, from 3.5 to 35, from 5 to 25, or from 6 to 20.

The composition may comprise at least one, in particular one, monosaccharide. Monosaccharide may be chosen from ribose, saccharose, fructose and glucose, in particular it is glucose.

Composition may comprise an amount of monosaccharide ranging from 1 à 12.5% by weight, from 1.5 to 10% by weight, from 2 to 8% by weight, from 2.5 to 7.5% by weight compared to the total weight, in particular dry weight, of the composition.

Composition may have a weight ratio collagen/monosaccharide ranging from 5 to 100, from 7 to 65, from 10 to 96/2, or from 11 to 40.

Monosaccharide, such as ribose, saccharose, fructose, glucose and their mixture, in particule glucose, may allow obtaining particles of collagen, more particularly fibrous and/or fibrillar, together with the monosaccharide having desired characteristics, in particular considering size and/or density.

According to an embodiment, the composition comprises, or consists in, particles comprising, or consisting of, collagen and monosaccharide(s).

According to a more specific embodiment, the composition comprises, or consists in:
  fibrous and/or fibrillar collagen, in an amount of around 85% by weight, thrombin ranging from 0.2 à2 UI/mg of composition, in particular dry, chondroitin sulfate, in an amount of around 10% by weight, and glucose, in an amount of around 4.9% by weight compared to the total weight, in particular dry weight, of the composition.

By <<an amount of around X %>>, is meant a variation of plus or minus 20%, for example an amount of around 10% means from 8 to 12%, in particular plus or minus 10%, more particularly plus or minus 5%.

The composition, in particular under dry from, may have a tapped density of at least 0.4 g/l, and/or an untapped density of at least 0.3 g/l. Preferably, the composition has a tapped density higher than 0.4 g/mL, most preferably ranging from 0.4 g/mL and 0.6 g/mL.

The composition, in particular dry, may comprise at least 50% by weight of the particules having a size ranging from 200 to 400 μm.

By "dry composition" or "composition under dry form", is meant a composition comprising a limited amount of solvent, in particular water. This amount may be less than 20% by weight, less than a 15% by weight, less than 10% by weight, less than 5% by weight compared to the total weight of the composition.

Thus then invention also concerns a kit comprising, or consisting of, a device according to the invention with a powder, in particular a haemostatic powder such as disclosed above.

BIBLIOGRAPHIC REFERENCE

EP 1 550 713

The invention claimed is:

1. A device for delivering a powder to a target site, said device comprising:
    a body;
    a powder storage filled with the powder to be delivered to the target site;
    a gas reservoir located within said body to be filled with a gas under pressure;
    an outlet nozzle communicating with said powder storage;
    a normally closed gas outlet valve located within said body between said gas reservoir and said powder storage and being closed to block the flow of gas under pressure from said gas reservoir to said powder storage; and
    an activation handle coupled to said normally closed gas outlet valve, said activation handle moving in a first direction relative to said body in response to a force applied to said activation handle for causing said normally closed gas outlet valve to open and thereby enable a blast of gas under pressure to be applied from said gas reservoir to said powder storage, whereby at least some of the powder from said powder storage is entrained and delivered to the target site by way of said outlet nozzle
    wherein it further comprises a normally open gas inlet valve located within said body between said gas reservoir and a source of gas under pressure and being opened to permit said gas reservoir to be filled with the gas under pressure from the source thereof; and
    wherein said activation handle is coupled to said normally open gas inlet valve to cause said normally open gas inlet valve to close and thereby prevent said gas reservoir from further receiving gas under pressure from said source when said activation handle moves in said first direction relative to said body in response to said force applied to said activation handle.

2. The device of claim 1, wherein the activation handle is both coupled to said normally closed gas outlet valve and said normally open gas inlet valve for, when said activation handle moves in the first direction relative to said body, simultaneously causing said normally open gas inlet valve to close and thereby block said gas reservoir from further receiving gas under pressure from said source, and causing said normally closed gas outlet valve to open and thereby enable a blast of gas under pressure to be applied from said gas reservoir to said powder storage, whereby at least some of the powder from said powder storage is entrained and delivered to the target site by way of said outlet nozzle.

3. The device of claim 1, further comprising a gas outlet hose running between said gas reservoir and said powder storage, said normally closed gas outlet valve coupled to said gas outlet hose and being closed so as to shut said gas outlet hose and thereby block the flow of gas under pressure from said gas reservoir to said powder storage, and said normally closed outlet valve being opened in response to the movement of said activation handle in said first direction so that said gas outlet hose is correspondingly opened to allow said blast of gas under pressure to be applied from said gas reservoir to said powder storage via said gas outlet hose.

4. The device of claim 1, wherein the normally closed gas outlet valve surrounds a gas outlet hose, said normally closed gas outlet valve having stationary and movable valve members between which said gas outlet hose is positioned, said stationary and movable valve members being positioned together when said normally closed gas outlet valve is closed in order to shut said gas outlet hose, and said stationary and movable valve members being positioned apart when said normally closed gas outlet valve is opened to correspondingly open said gas outlet hose.

5. The device of claim 4, further comprising a spring located within said body and communicating with said normally closed gas outlet valve, said spring being compressed when said activation handle moves in said first direction relative to said body in response to the force applied to said handle for causing the stationary and movable valve members of said normally closed gas outlet valve to be positioned apart and said outlet valve to be opened, and said spring expanding when the force applied to said activation handle is terminated for causing said stationary and movable valve members to be positioned together and said outlet valve to be closed.

6. The device of claim 1, further comprising a spring surrounding a movable valve member of said normally closed gas outlet valve, said spring generating a pushing force against said movable valve member for urging said movable valve member to move relative to a stationary valve member of said normally closed gas outlet valve, and said activation handle to rotate in an opposite direction relative to said body when the force applied to said handle is terminated and said spring expands.

7. The device of claim 1, wherein the activation handle is depressed and rotated inwardly of said body when said handle moves in said first direction relative to said body in response to the force applied to said handle, and wherein the device further comprises a pivot pin attached to said activation handle and a pivot post attached to said body within which said pivot post is pivotally received, said pivot pin rotating at said pivot post and said activation handle rotating inwardly of said body when said handle moves in said first direction in response to the force applied thereto.

8. The device of claim 1, further comprising a gas inlet hose attached at one end thereof to said gas reservoir and adapted to be connected at the opposite end to the source of gas under pressure, said normally open gas inlet valve being coupled to said gas inlet hose and being closed in response to the force applied to said activation handle and the movement of said activation handle in said first direction so as to shut said gas inlet hose and thereby block the flow of gas under pressure from said source thereof to said gas reservoir via said gas inlet hose, and said normally open gas inlet valve being opened when the force applied to said activation handle is terminated so that said gas inlet hose is correspondingly opened to allow said gas reservoir to be filled with the gas under pressure from said source via said gas inlet hose.

9. The device of claim 1, further comprising a gas inlet hose attached at one end thereof to said gas reservoir and adapted to be connected at the opposite end to the source of gas under pressure, wherein the normally open gas inlet valve includes a hose pinching member attached to and movable with said activation handle, said hose pinching member moving towards and into contact with said gas inlet hose so that said gas inlet hose is shut and the flow of gas under pressure from said source thereof to said gas reservoir via said gas inlet hose is blocked when said activation handle moves in said first direction in response to the force applied thereto.

10. The device of claim 1, wherein said powder storage includes a plurality of powder-filled chambers, each chamber being filled with a supply of powder to be delivered to the target site, a particular one of said powder-filled chambers of said powder storage being located in a fluid path between said gas reservoir and said outlet nozzle so that the powder contents of said particular one chamber is entrained by said blast of gas when said activation handle is moved in said first direction in response to the force applied thereto.

11. The device of claim 10, wherein the powder storage is rotatable to be positioned so that only one at a time of said plurality of powder-filled chambers of said powder storage is located in said fluid path.

12. The device of claim 11, further comprising a ratchet wheel located within said body and coupled to said powder storage, said ratchet wheel being rotated in response to said activation handle moving in said first direction relative to said body in response to the force applied to said handle for imparting a corresponding rotation to said powder storage until the particular one of said plurality of powder-filled chamber is rotated into said fluid path.

13. The device of claim 12, further comprising a ratchet actuator projecting from said activation handle and communicating with said ratchet wheel, such that a movement of said activation handle in said first direction causes a corresponding movement of said ratchet actuator and a rotation of each of said ratchet wheel and said powder storage to which said ratchet wheel is coupled, whereby the particular one of said plurality of powder-filled chambers of said powder storage is rotated into said fluid path.

14. The device of any of claim 12 or 13, further comprising a cover located between said body and said outlet nozzle and enclosing said powder storage, said cover having a back cap extending thereacross and a hole formed through said cover, said ratchet wheel coupled to said powder storage by way of a shaft extending through said hole and between said ratchet wheel and said powder storage, whereby a rotation of said ratchet wheel within said body is transferred to the powder storage enclosed by said cover by way of said shaft.

15. The device of claim 14, further comprising a back cap which is detachably connected to said cover by means of flexible snaps projecting from said back cap for the removable receipt by respective locking slots formed in said cover.

16. The device of claim 11, further comprising a cover including a flexible index tab projecting therefrom and communicating with said powder storage enclosed by said cover, said index tab limiting the rotation of said powder storage so that successive ones of said plurality of powder filled chambers of said powder storage are moved one at a time into said fluid path between said gas reservoir and said outlet nozzle.

17. The device of claim 16, further comprising a back cap of said cover which has serially connected gas channels running horizontally and vertically therethrough, said gas channels lying in said fluid path between said gas reservoir and said outlet nozzle.

18. The device of claim 1, further comprising a powder storage enclosed by a cover which has at least one inlet seal extending across one end thereof to seal first ends of the plurality of powder-filled chambers of said powder storage and at least one outlet seal extending across the opposite end thereof to seal the opposite ends of said powder-filled chambers, each of said inlet and outlet seals having a hole formed therethrough and lying in said fluid path between said gas reservoir and said outlet nozzle.

19. The device of claim 1, further comprising a pressure relief valve provided within the gas reservoir to allow gas to escape from the gas reservoir when the gas pressure within the gas reservoir exceeds a threshold pressure while said normally gas outlet valve is in a closed position.

20. A kit comprising a haemostatic composition in form of powder and comprising collagen, and a device for delivering said powder to a target site, wherein said device comprises:
 a body;
 a powder storage filled with the powder to be delivered to the target site;
 a gas reservoir located within said body to be filled with a gas under pressure;
 an outlet nozzle communicating with said powder storage;
 a normally closed gas outlet valve located within said body between said gas reservoir and said powder storage and being closed to block the flow of gas under pressure from said gas reservoir to said powder storage; and
 an activation handle coupled to said normally closed gas outlet valve, said activation handle moving in a first direction relative to said body in response to a force applied to said activation handle for causing said normally closed gas outlet valve to open and thereby enable a blast of gas under pressure to be applied from said gas reservoir to said powder storage, whereby at least some of the powder from said powder storage is entrained and delivered to the target site by way of said outlet nozzle
 wherein it further comprises a normally open gas inlet valve located within said body between said gas reservoir and a source of gas under pressure and being opened to permit said gas reservoir to be filled with the gas under pressure from the source thereof; and
 wherein said activation handle is coupled to said normally open gas inlet valve to cause said normally open gas inlet valve to close and thereby prevent said gas reservoir from further receiving gas under pressure from said source when said activation handle moves in said first direction relative to said body in response to said force applied to said activation handle.

* * * * *